United States Patent
Afargan et al.

(10) Patent No.: US 9,468,758 B2
(45) Date of Patent: Oct. 18, 2016

(54) WOUND DIAGNOSIS

(71) Applicant: E-qure Corp., New York, NY (US)

(72) Inventors: Michel Afargan, Ra'anana (IL); Elia Bernardino Ricci, Cascinette d'Vrea (IT); Itshak Y. Ben-Yesha, Shilat (IL)

(73) Assignee: E-QURE CORP., New York, NY (US)

( * ) Notice: Subject to any disclaimer, the term of this patent is extended or adjusted under 35 U.S.C. 154(b) by 0 days.

(21) Appl. No.: 14/472,445

(22) Filed: Aug. 29, 2014

(65) Prior Publication Data

US 2014/0371620 A1 Dec. 18, 2014

Related U.S. Application Data

(63) Continuation-in-part of application No. 12/477,944, filed on Jun. 4, 2009, now Pat. No. 8,855,779.

(60) Provisional application No. 61/118,451, filed on Nov. 27, 2008.

(51) Int. Cl.
*A61N 1/32* (2006.01)
*A61N 1/36* (2006.01)
(Continued)

(52) U.S. Cl.
CPC ............... *A61N 1/326* (2013.01); *A61B 5/04* (2013.01); *A61B 5/05* (2013.01); *A61B 5/445* (2013.01); *A61B 5/7257* (2013.01); *A61B 5/7282* (2013.01); *A61N 1/36014* (2013.01)

(58) Field of Classification Search
CPC .... A61N 1/326; A61N 1/36014; A61B 5/04; A61B 5/05; A61B 5/445; A61B 5/7257; A61B 5/7282
See application file for complete search history.

(56) References Cited

U.S. PATENT DOCUMENTS 4,754,763 A    7/1988  Doemland
6,061,597 A *  5/2000  Rieman .................... A61N 1/40
                                                          607/51

(Continued)

FOREIGN PATENT DOCUMENTS

JP    H02005925 A    1/1990
JP    2005095384 A   4/2005

(Continued)

OTHER PUBLICATIONS

I. S. Foulds and A. T. Barker, Human skin battery potentials and their possible role in wound healing, British Journal Dermatology 1983, pp. 515-522.

(Continued)

*Primary Examiner* — Catherine Voorhees
(74) *Attorney, Agent, or Firm* — Roach Brown McCarthy & Gruber, P.C.; Kevin D. McCarthy

(57) ABSTRACT

A device for diagnosing a wound in a patient, the device comprising: at least two electrodes configured to be placed on the skin of the patient, wherein the at least two electrodes are placed in the vicinity of the wound; and at least one signal processor operatively coupled with the at least two electrodes, wherein the at least one signal processor is configured to: i) detect and record an endogenous alternating electrical signal in an area of the wound, ii) transform said endogenous alternating electrical signal into a voltage versus frequency spectrum using a Fast Fourier Transform (FFT) algorithm, and iii) diagnose the wound as a chronic wound if the voltage for a frequency between 65-200 Hz of the frequency spectrum is below $10^{-7.3} \pm 10\%$ volts and as an acute wound if the voltage for a frequency between 65-200 Hz of the frequency spectrum is above $10^{-7.3} \pm 10\%$ volts.

20 Claims, 3 Drawing Sheets

(51) Int. Cl.
A61B 5/00 (2006.01)
A61B 5/04 (2006.01)
A61B 5/05 (2006.01)

(56) References Cited

U.S. PATENT DOCUMENTS

| | | | |
|---|---|---|---|
| 6,213,934 B1 | 4/2001 | Bianco et al. | |
| 6,363,284 B1* | 3/2002 | Nachum | A61N 1/326 128/898 |
| 6,941,173 B2* | 9/2005 | Nachum | A61N 1/36021 128/898 |
| 7,010,353 B2* | 3/2006 | Gan | A61N 1/326 607/50 |
| 7,016,737 B2* | 3/2006 | Petrofsky | A61N 1/326 607/50 |
| 8,855,779 B2 | 10/2014 | Afargan et al. | |
| 2002/0019023 A1 | 2/2002 | Dasseux et al. | |
| 2005/0107718 A1 | 5/2005 | Hashimshony | |
| 2006/0270942 A1 | 11/2006 | McAdams | |
| 2009/0012584 A1 | 1/2009 | Nachum | |
| 2010/0030058 A1 | 2/2010 | Mammone et al. | |
| 2010/0131031 A1 | 5/2010 | Afargan et al. | |
| 2012/0157875 A1* | 6/2012 | Afargan | A61B 5/4076 600/547 |

FOREIGN PATENT DOCUMENTS

| | | |
|---|---|---|
| JP | 2006508732 A | 3/2006 |
| WO | 9701372 | 1/1997 |

OTHER PUBLICATIONS

Sue E. Gardner, Rita A. Frantz, Frank L. Schmidt, Effect of electrical stimulation on chronic would healing: a meta-analysis, Blackwell Synergy—Wound Repair Regen, Nov. 1999, vol. 7 Issue 6, p. 495.

Luther C. Kloth, Electrical Stimulation for Would Healing: A Review of Evidence From In Vitro Studies, Animal Experiments, and Clinical Trials, Lower Extremity Wounds 2005, pp. 23-44.

Colin D. McCaig, Ann M. Rajnicek, Bing Song, Min Zhao, Controlling Cell Behavior Electrically: Current Views and Future Potential, Physiological Reviews Published, Jul. 1, 2005, vol. 85, pp. 943-978.

Frank Moss, Lawrence M. Ward, Walter G. Sannita, Stochastic resonance ans sensory information processing: a tutorial and review of application, Clinical Neurophysiology, 2004, pp. 267-281.

Alain Destexhe et al., Neuronal Computations with Stochastic Network States, Science, Oct. 6, 2006, pp. 85-90.

Ilya L. Kruglikov and Hermann Dertinger, Stochastic Resonance as a Possible Mechanism of Ampliication of Weak Electric Signals in Living Cells, Bioelectromagnetics, 1994, pp. 539-547.

Amber T Collins, J Troy Blackburn, Chris W Olcott, Douglas R Dirschl, Paul S Weinhold, The effects of stoastic resonance electrical stimulation and neoprene sleeve on knee proprioception, Journal of Orthopedic Surgery and Research 2009.

Neel T. Dhruv, James B. Niemi, Jason D. Harry, Lewis A Lipsitz, James J. Collins, Enhancing tactile sensation in older adults with electrical noise stimulation, Somatosensory Systems, Pain, Neuroreport, vol. 13 No. 5 Apr. 16, 2002, pp. 597-600.

Wen Liu, Lewis A. Lipsitz, Jonathan Bean, D. Casey Kerrigan, James J. Collins, Noise-Enhanced Vibrotactile Sensitivity in Older Adults, Patients With Stroke, and Patients With Diabetic Neuropathy, Arch Phys Med Rehabil vol. 83, Feb. 2002, pp. 171-176.

Shigeo M. Tanaka, Imranul M. Alam, Charles H. Turner, Stochastic resonance in osteogenic response to mechanical loading, The FASEB Journal, vol. 17 Feb. 2003, pp. 313-314.

Frank T. Padberg Jr., Allen H. Maniker, Gwendolyn Carmel, Peter J,. Pappas, Michael B. Silva Jr., Robert W. Hobson II, Sensory impairment: A feature of chronic venous insufficiency, Journal of Vascular Surgery, Nov. 1999, vol. 30, pp. 836-843.

E. Ricci, M afaragan, The effect of stochastiv electrical noise on hard-to-heal wounds, Journal of Wound Care vol. 1 9 , No. 3 , Mar. 2010, pp. 96-103.

Steven P. Keller, Alfred W. Sandrock, Shai N. Gozani, Noninvasive Detection of Fibrillation Potentials in Skeletal Muscle, IEEE Transactions on Biomedical Engineering, vol. 49, No. 8, Aug. 2002, pp. 788-795.

Dome R. Yager, Liang-Y. Zhang, Hui-Xiu Liang, Robert F. Diegelmann, I. Kelman Cohen, Wound Fluids from Human Pressure Ulcers Contain Elevated Matrix Metalloproteinase Levels and Activity Compared to Surgical Would Fluids, The Society for Investigative Dermatology, Inc. 1996, pp. 743-748.

Gerald S. Lazarus, Diane M. Cooper, David R. Knighton, David J. Margolis, Roger E. Percoraro, George Rodeheaver, Martin C. Robson, Definitions and guidelines for assessment of wounds and evaluation of healing, Wound Repair and Regeneration, Jul.-Sep. 1994, vol. 2, pp. 165-170.

Peter N. Steinmetz, Amit Manwani, Christof Koch, Subthreshold Voltage Noise Due to Channel Fluctuations in Active Neuronal Membranes, Journal of Computational Neuroscience, 2000, pp. 133-148.

Leila Chaieb, Gyula Kovacs, Csaba Cziraki, Mark Greenlee, Walter Paulus, Andrea Antal, Short-duration transcranial random noise stimulation induces blood oxygenation level dependent response attenuation in the human motor cortex, Aug. 2, 2009, Exp Brain Res, pp. 439-444.

Dabiella Terney, Leila Chaieb, Vera Moliadze, Andrea Antal, Walter Paulus, Increasing Human Brain Excitability by Transcranial Frequency Random Noise Stimulation, The Journal of Neuroscience, Dec. 24, 2008, pp. 14147-14155.

Rashmi Kumari, Lisa B Willing, J Kyle Krady, Susan J Vannucci, Ian A Simpson, Impaired wound healing after cerebral hypoxia-ischemia in the diabetic mouse, Journal of Cerebral Blood Flow & Metabolism, 2007, pp. 710-718.

Dirk Roosterman, Tobias Goerge, Stefan W. Schneider, Nigel W. Bunnett, Martin Steinhoff, Neuronal Control of Skin Function: The Skin as a Neuroimmunoendocrine Organ, American Physiological Society, 2006, pp. 1309-1379.

* cited by examiner

WOUND DIAGNOSIS

BACKGROUND

The present invention relates to the field of diagnosis of wounds in a live tissue.

Electrophysiology is the science and branch of physiology that delves into the flow of ions in biological tissues, the electrical recording techniques which enable the measurement of this flow and their related potential changes. One system for such a flow of ions is the Power Lab System by ADInstruments headquartered in Sydney, Australia. Clinical applications of extracellular recording include among others, the electroencephalogram and the electrocardiogram.

Deterministic signals are exactly predictable for the time span of interest. Deterministic signals can be described by mathematical models. Stochastic or random signals are those signals whose value has some element of chance associated with it, therefore it cannot be predicted exactly. Consequently, statistical properties and probabilities must be used to describe stochastic signals. In practice, biological signals often have both deterministic and stochastic components.

Signal amplitude statistics may be characterized by a number of statistics may be used as a measure of the location or "centre" of a random signal. These may include mean, median, mode, maximal and minimal amplitude, range and peak to peak amplitude of the signal.

There are quantitative methods to measure the frequency and amplitude of a waveform. One of the most well known is spectral analysis, which mathematically decomposes the waveform into a sum of different waveforms. Fourier analysis decomposes the waveform into different frequency components and measures the amplitude (power) of each frequency component.

Whereas research on direct current (DC) activity in wound healing and tissue remodeling has a long history, electric fields of alternating current (AC) with specific frequencies have been much less studied.

Specific frequencies have been detected in various biological pathways known to be associated with wound healing such as pain, cell metabolism inter-cellular communication and bone growth.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided in accordance with an embodiment, a device for diagnosing a wound in a patient, the device comprising: at least two electrodes configured to be placed on the skin of the patient, in the vicinity of the wound; and at least one signal processor operatively coupled with the at least two electrodes, wherein the at least one signal processor is configured to: detect and record an endogenous alternating electrical signal in an area of the wound, transform said endogenous alternating electrical signal into a voltage versus frequency spectrum using a Fast Fourier Transform (FFT) algorithm, and diagnose the wound as a chronic wound if the voltage for a frequency between 65-200 Hz of the frequency spectrum is below $10^{-7.3} \pm 10\%$ volts and as an acute wound if the voltage for a frequency between 65-200 Hz of the frequency spectrum is above $10^{-7.3} \pm 10\%$ volts.

There is provided in accordance with another embodiment, a method for diagnosing a wound in a patient, the method comprising: detecting and recording an endogenous alternating electrical signal in an area of the wound; transforming said endogenous alternating electrical signal into a voltage versus frequency spectrum using a Fast Fourier Transform (FFT) algorithm; and diagnosing said wound as a chronic wound if the voltage for a frequency between 65-200 Hz of the frequency spectrum is below $10^{-7.3} \pm 10\%$ volts and as an acute wound if the voltage for a frequency between 65-200 Hz of the frequency spectrum is above $10^{-7.3} \pm 10\%$ volts.

There is provided in accordance with yet another embodiment, a method for diagnosing a wound in a patient, the method comprising: receiving an endogenous alternating electrical signal recorded in an area of the wound; transforming said endogenous alternating electrical signal into a voltage versus frequency spectrum using a Fast Fourier Transform (FFT) algorithm; and diagnosing said wound as a chronic wound if the voltage for a frequency between 65-200 Hz of the frequency spectrum is below $10^{-7.3} \pm 10\%$ volts and as an acute wound if the voltage for a frequency between 65-200 Hz of the frequency spectrum is above $10^{-7.3} \pm 10\%$ volts.

In some embodiments, the at least one signal processor is selected from the group consisting of: an analog signal processor and a digital signal processor.

In some embodiments, the at least two electrodes are placed on opposing sides of the wound.

In some embodiments, the at least two electrodes are placed on the most distant opposing sides of the wound.

In some embodiments, the device further comprises a signal generator configured to deliver electrical currents to an area of said wound if said wound is diagnosed as a chronic wound.

In some embodiments, said electrical currents are selected from the group consisting of: alternating electrical currents and pulsed electrical currents.

In some embodiments, the device further comprises an amplifier configured to amplify readings of the endogenous alternating electrical signal.

In some embodiments, the diagnosing of the wound comprises diagnosing the wound as a chronic wound if the voltage for a frequency between 100-150 Hz of the frequency spectrum is below $10^{-7.3} \pm 10\%$ volts and as an acute wound if the voltage for a frequency between 100-150 Hz of the frequency spectrum is above $10^{-7.3} \pm 10\%$ volts.

In some embodiments, immediately before and during the detection and recording of the endogenous electrical signal, no electrical stimulation is applied to the patient.

In some embodiments, the detecting and recording of said endogenous alternating electrical signal and the transforming of said endogenous alternating electrical signal into a voltage versus frequency spectrum are performed by using at least one signal processor.

In some embodiments, the detecting and recording of the endogenous alternating electrical signal in the area of the wound further comprises placing at least two electrodes in the vicinity of the wound, wherein the at least two electrodes are operatively coupled with the at least one signal processor.

In some embodiments, the placing of the at least two electrodes comprises placing the at least two electrodes on opposing sides of the wound.

In some embodiments, the placing of the at least two electrodes comprises placing the at least two electrodes on the opposing and most distant sides of the wound.

In some embodiments, the method further comprises determining a therapy for the wound based on the diagnosing of said wound as a chronic wound or as an acute wound.

In some embodiments, the therapy is an electrical therapy.

In some embodiments, the method further comprises delivering electrical currents to the wound if the wound is diagnosed as a chronic wound.

In some embodiments, the transforming of said endogenous alternating electrical signal into a voltage versus frequency spectrum are performed by using at least one signal processor.

In some embodiments, the determining of the therapy for the wound comprises determining an electrical therapy for the wound if the wound is diagnosed as a chronic wound.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Methods and devices for wound diagnosis are disclosed herein. The disclosed wound diagnosis may provide diagnosis of damaged live tissue by detection of an endogenous electrical alternating current flow through the tissue. The disclosed wound diagnosis may provide techniques for measuring and analyzing the electrical field in areas of a live damaged body tissue and in particular, for diagnosing a wound as a chronic or as an acute based on its discrete electrical profile. Such diagnosis may be utilized, for example, to determine a suitable treatment, including an electrical therapy.

The term "chronic wound", as referred to herein, may relate to a wound which does not exhibit any signs of healing in a predefined time.

The term "acute wound", as referred to herein, may relate to wounds which exhibit signs of healings in a predefined time.

The term "wounds", as referred to herein, may relate to acute wounds and chronic wounds, such as ulcers.

Figure 1:
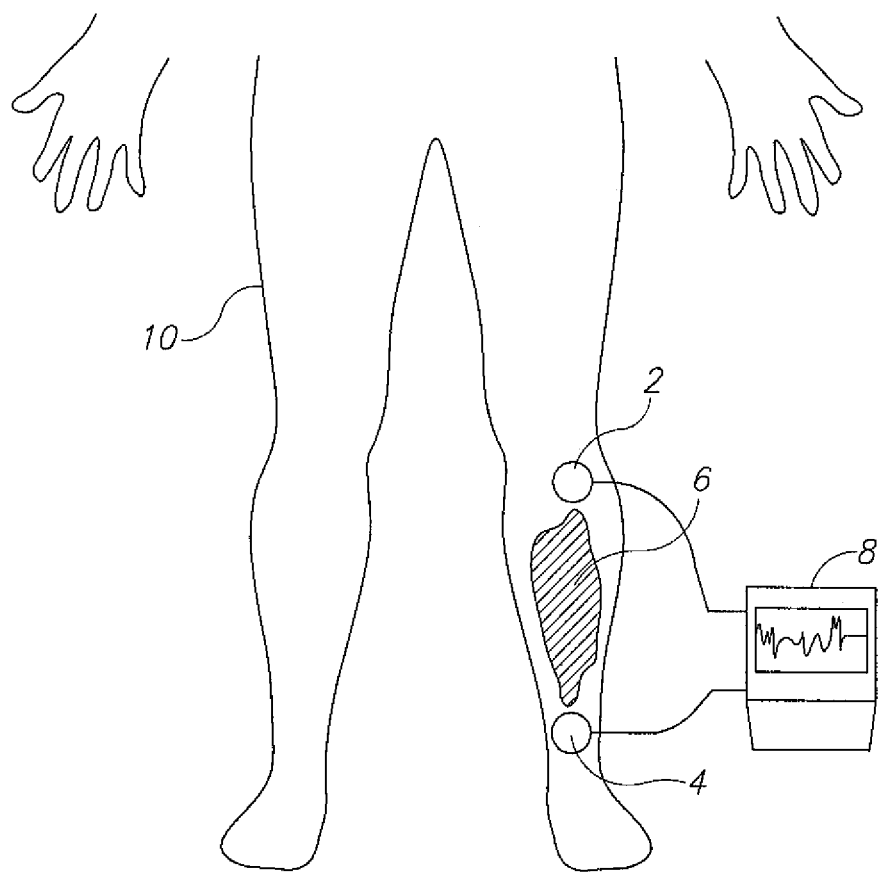
FIG. 1 shows an illustration of a device including electrodes placed on a skin of a patient in the vicinity of a wound according to an embodiment.

Reference is now made to FIG. 1, which shows an illustration of a device 8 including electrodes placed on a skin of a patient in the vicinity of a wound according to an embodiment.

Device 8 may include two electrodes 2 and 4, and a signal processor (not shown). Device 8 may include an amplifier such as a common mode rejection amplifier, which enables the amplification of readings of the endogenous alternating electrical signal, i.e., nanovolt (nV) readings of the electrical fields around wound 6. The signal processor may be operatively coupled with electrodes 2 and 4. Electrodes 2 and 4 may be configured to be placed on the skin of a patient 10. Electrodes 2 and 4 may be placed in the vicinity of an exemplary wound 6 in a leg of patient 10 as shown in FIG. 1. Optionally, device 8 may include more than two electrodes.

Electrodes 2 and 4 may be advantageously placed on two opposing sides of wound 6, which are optionally the most distant from one another. This may allow a better recording of endogenous alternating electrical signals flowing through wound 6, since a maximal wound area exists between the electrodes. For example, electrodes 2 and 4 may be placed at two opposing sides of a medial axis of wound 6 as shown in FIG. 1. Electrodes 2 and 4 may be, for example, soft surface E.C.G. electrodes (e.g., MLA1010B by AD Instruments Pty Ltd., Australia). In some other embodiments, electrodes 2 and 4 may be placed in various locations around the wound, not in opposing sides of the wound.

The signal processor may be an analog signal processor or a digital signal processor. The signal processor may be configured to detect and record an endogenous alternating electrical signal in an area of wound 6 and transform the endogenous alternating electrical signal into a voltage versus frequency spectrum using a Fast Fourier Transform (FFT) algorithm. Optionally, the signal processor may be configured to diagnose wound 6 as a chronic or as an acute wound. The signal processor may perform the above operations in accordance with the method of FIG. 3. Optionally, device 8 may include one or more signal processors configured to perform the above operations.

Device 8 may be an Alternating Current (AC) recorder such as the PowerLab-4/30-PRO System (AD Instruments Pty Ltd Australia 2153) consisting of the BioAmp ML132 amplifier with a common mode rejection ration (CMRR) of 85 db. Various sampling rates may be used such as 2,000 samples per second, 5,000 or 10,000 per second, or any other higher or lower sampling rates.

In some embodiments, device 8 may be or may be embedded in an electrical stimulating system for providing treatment to wound 6. The electrical stimulating system (or device 8) may include electrodes 2 and 4 and the signal processor. The signal processor may be configured to detect and record the alternating electrical signal in an area of wound 6 and transform the signal into a voltage versus frequency spectra using an FFT algorithm. The signal processor may be then further configured to use a resultant FFT level to generate data regarding a current state of wound 6 (i.e., diagnose the wound as chronic or acute) and transmit the data to a component of the electrical stimulating system configured to provide electrical stimulation. Such a component may include a signal generator configured to deliver an electrical current to wound 6, such that the characteristics of the electrical current delivered are determined by the data regarding the current state of the wound (i.e., the diagnosis of the wound as an acute wound or as a chronic wound). In general, the signal generator and the delivering of the electrical current to the patient's body may be according to prior art devices and techniques for generating electrical stimulation for wound therapy. Such devices and methods may be found, for example, in U.S. Pat. No. 8,112,156.

Figure 2:
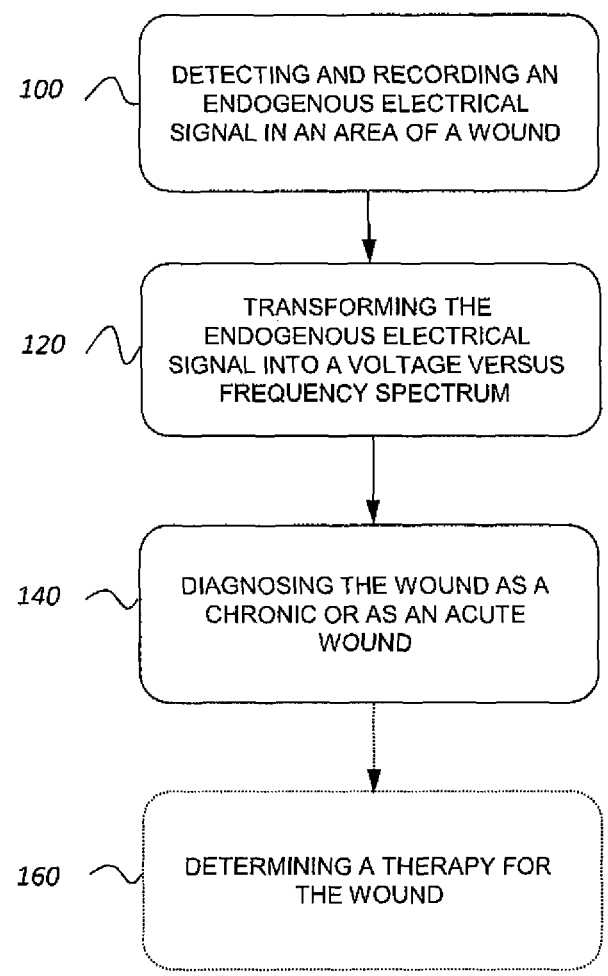
FIG. 2 shows a flowchart of a method for diagnosing a wound in a patient, constructed and operative in accordance with an embodiment of the disclosed techniques.

Reference is now made to FIG. 2, which shows a flowchart of a method for diagnosing a wound in a patient, constructed and operative in accordance with an embodiment of the disclosed techniques.

In a step 100, an endogenous alternating electrical signal is detected and recorded in an area of the wound. The detection and recording of the alternating electrical signal may be performed by using at least one signal processor. No electrical stimulation may be applied to the patient immediately before and during the detection and recording of the endogenous alternating electrical signal. The detection and recording of the endogenous alternating electrical signal may be made without providing any electrical stimulation to the patient, for example during at least 5, 10, 30 or 60 minutes before performing the detection and recording—which durations may be referred to as immediately before the detection and recording.

The detection and recording of the endogenous alternating electrical signal may then further include placing at least two electrodes in the vicinity of the wound. The at least two electrodes may be operatively coupled with the at least one signal processor. In some embodiments, the at least two electrodes may be placed on two opposing sides of the wound. In some embodiments, the at least two electrodes may be placed on the two opposing and most distant sides of the wound, in order to enhance the recording of the endogenous alternating electrical signals flowing through the wound. In some other embodiments, the electrodes may be placed in various locations around the wound and not necessarily in exact opposing sides of the wound.

In some embodiments, the at least two electrodes may be placed at least 10 millimeters (mm) away from the edge of the wound in order to prevent peeling off the edge skin when peeling off the electrodes. In other embodiments, the at least two electrodes may be placed closer or farther away from the edge of the wound.

In some embodiments, alternatively to steps 100 and 110, an endogenous alternating electrical signal recorded in an area of the wound may be received.

In a step 120, the endogenous alternating electrical signal may be transformed into a voltage versus frequency spectrum using an FFT algorithm. The transforming of the endogenous alternating electrical signal may be performed by using at least one signal processor as known in the art.

In a step 140, the wound may be diagnosed as a chronic wound if the voltage in a frequency range between 65-200 Hertz (Hz) of the frequency spectrum is below a certain threshold, and as an acute wound, if the voltage in the same frequency is above that certain threshold. In some embodiments, the threshold is $10^{-7.3}$ volts. In other embodiments, the threshold is up to 10% higher or lower than $10^{-7.3}$ volts (namely, it can be defined as $10^{-7.3} \pm 10\%$ volts). The diagnosis may be performed automatically, by the signal processor, or manually, by a caregiver. The threshold of $10^{-7.3} \pm 10\%$ volts was determined according to experimental results which will be detailed herein below.

In other embodiments, the diagnosing of the wound as a chronic or an acute wound may be made based on the aforesaid threshold but in a frequency range between 65-150 Hz. In other embodiments, the diagnosing of the wound as a chronic or an acute wound may be made based on the aforesaid threshold but in a frequency range between 80-150 Hz. In other embodiments, the diagnosing of the wound as a chronic or an acute wound may be made based on the aforesaid threshold but in a frequency range between 100-150 Hz. In other embodiments, the diagnosing of the wound as a chronic or an acute wound may be made based on the aforesaid threshold but in a frequency range between 100-140 Hz. In other embodiments, the diagnosing of the wound as a chronic or an acute wound may be made based on the aforesaid threshold but in a frequency range between 100-180 Hz.

In some embodiments, in order to reduce to a minimum the effect of environmental electromagnetic radiation, the detection and recording of the endogenous alternating electrical signal may be conducted in an isolated room with no fluorescent lights, cell phones or any other electronic devices which emit substantial electromagnetic radiation. In some embodiments, the patient may be requested to recline in a supine position for several minutes (e.g., ten minutes) before the detection and recording and/or may be asked to move minimally during the detection and recording phase. In some embodiments, in order to reduce the possible effect of electrode-skin impedance variability, the area of the skin of the patient on which the electrodes are to be placed may be gently abraded by using abrasive gel (e.g., NuPrep, MLA1093B, ADIntruments Pty Ltd., Australia).

In an optional step 160, a therapy for the wound based on the diagnosing of said wound as a chronic wound or as an acute wound may be determined. The therapy may be an electrical therapy, negative pressure therapy, hyperbaric oxygen therapy, growth agent therapy, etc.

For electrical therapy, the determining of the therapy for the wound may include determining that electrical therapy is needed only if the wound is chronic, since electrical therapy may have little or no effect on acute wounds. Therefore, in the case of a chronic wound, the method may include performing electrical therapy by delivering electrical currents such as pulsed electrical currents or alternating electrical currents at a few volts up to 120 volts to the wound, using the aforesaid electrodes disposed around the wound, or different electrodes (e.g. one or more electrodes in the wound itself and one or more electrodes external to the wound). The alternating currents may be stochastic and/or systematic.

The disclosed method may be executed, partially or entirely by the disclosed device.

EXPERIMENTAL RESULTS

Electrodermal activity in humans was measured using a spectral analysis of skin surface voltages and showed that wounds exhibit specific endogenous nanovolt stochastic currents having a broadband frequency spectrum of up to 1000 Hz. The experiment included 13 patients with chronic wounds and 8 patients with acute wounds.

To measure the electrical fields around wounds, a common mode rejection amplifier was used, which enables the amplification of nanovolt (nV) readings. For these electrical recordings, two electrodes were placed on both proximal and distal sides across the medial axis of the injured skin, and the raw current outputs were measured against a ground electrode. In order to assess the specificities of the recorded stochastic currents, their spectral distribution was measured in the 1 Hz to 1 Kilohertz bandwidth. The 48 to 52 Hz frequency band was ignored to avoid any effects induced by external, environmental AC currents.

To establish the baseline levels for the electrical measurements, 22 healthy subjects (i.e., with no chronic or acute wounds) were enrolled and their mean logFFTs spectral distribution served as a baseline for comparisons.

To study endogenous electrical frequencies in damaged tissue, the same protocol of simultaneous (right arm and both legs) electrical measurements was conducted on patients with wounds. The mean electrical current of all wounds showed that patients with wounds had a significantly increased endogenous stochastic noise (p<0.0001) with a well defined spectral profile above the current baseline of intact skin from healthy subjects. The spectral profile of wounds displayed a stochastic white current within a frequency spectrum of 10 to 200 Hz followed by voltage decay from 200 to 750 Hz (pink noise).

Figure 3:
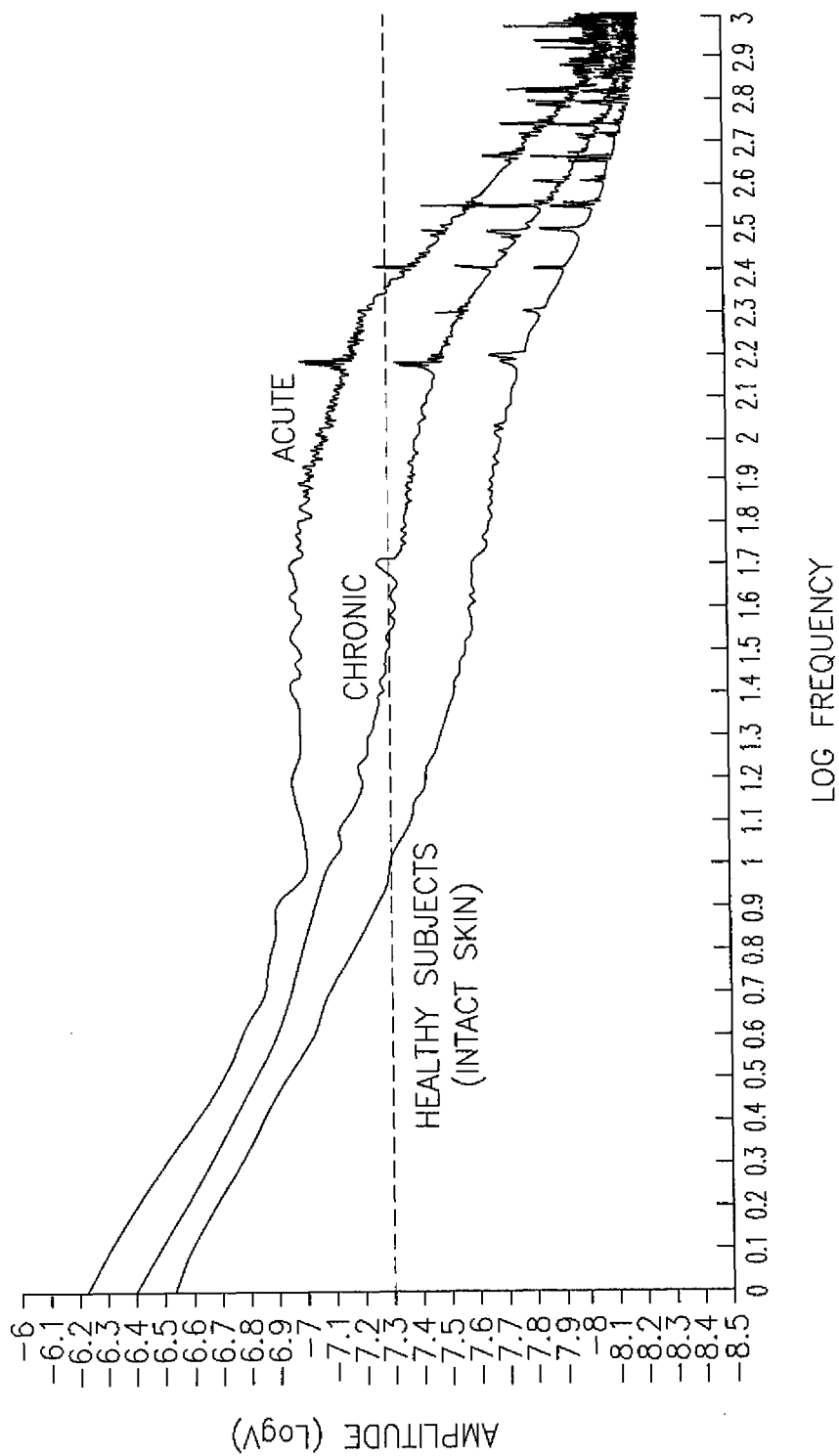
FIG. 3 shows graphs of mean log spectral densities vs. amplitude (log voltage) of measured skin currents in patients with chronic wounds, patients with acute wounds and in healthy patients.

Reference is now made to FIG. 3, which shows graphs of mean log spectral densities Vs amplitude (log voltage) of measured skin currents in patients with chronic wounds, patients with acute wounds and in healthy patients. The log frequency and the log voltage are the logarithms of frequency and voltage, correspondingly, with respect to base 10.

The mean log spectral densities of the skin currents were measured in acute and chronic wounds over multiple frequency bands of 1 to 10, 10 to 100, 100 to 200, 200 to 300, 400 to 600 and 600 to 1000 Hz. It was found that acute wounds (n=8) exhibit mean stochastic currents with a significantly higher amplitude than chronic wounds (p=0.05). The mean area under the voltage vs. frequency curve (AUC) of acute wound signal (AUC–36.5±6.2 micro Volt, n=8) is significantly above the mean AUC of chronic wounds (p=0.05). In other words, during the healing of wounds, stochastic random currents centered at a frequency of 100 Hz may be triggered by the body. A possible explanation for the source of this signal may be that neurons may induce this endogenous noise in order to increase the sensitivity of the wounded area to specific neural signals.

As one may see, a threshold of $10^{-7.3}\pm10\%$ volts for a frequency between 65-200 Hz is demonstrated which distinguishes between patients with acute wounds and patients with chronic wounds. Measurements in patients with chronic wounds exhibit voltage below the threshold of $10^{-7.3}\pm10\%$ volts and measurements patients with acute wounds exhibit voltage above the threshold of $10^{-7.3}\pm10\%$ volts, in that frequency range.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device for diagnosing a wound in a patient, the device comprising:
   at least two electrodes configured to be placed on the skin of the patient, in the vicinity of the wound; and
   at least one signal processor operatively coupled with the at least two electrodes, wherein the at least one signal processor is configured to:
   i) detect and record an endogenous alternating electrical signal in an area of the wound,
   ii) transform said endogenous alternating electrical signal into a voltage versus frequency spectrum using a Fast Fourier Transform (FFT) algorithm, and
   iii) diagnose the wound as a chronic wound when the voltage for a frequency between 65-200 Hz of the frequency spectrum is below $10^{-7.3}\pm10\%$ volts and as an acute wound when the voltage for a frequency between 65-200 Hz of the frequency spectrum is above $10^{-7.3}\pm10\%$ volts.

2. The device of claim 1, wherein the at least one signal processor is selected from the group consisting of: an analog signal processor and a digital signal processor.

3. The device of claim 1, wherein the at least two electrodes are placed on opposing sides of the wound.

4. The device of claim 1, wherein the at least two electrodes are placed on the most distant opposing sides of the wound.

5. The device of claim 1, further comprising a signal generator configured to deliver electrical currents to an area of said wound when said wound is diagnosed as a chronic wound.

6. The device of claim 5, wherein said electrical currents are selected from the group consisting of: alternating electrical currents and pulsed electrical currents.

7. The device of claim 1, further comprising an amplifier configured to amplify readings of the endogenous alternating electrical signal.

8. The device of claim 1, wherein the diagnosing of the wound comprises diagnosing the wound as a chronic wound when the voltage for a frequency between 100-150 Hz of the frequency spectrum is below $10^{-7.3}$ volts and as an acute wound when the voltage for a frequency between 100-150 Hz of the frequency spectrum is above $10^{-7.3}$ volts.

9. The device of claim 1, wherein immediately before and during the detection and recording of the endogenous electrical signal, no electrical stimulation is applied to the patient.

10. A method for diagnosing a wound in a patient, the method comprising:
    detecting and recording an endogenous alternating electrical signal in an area of the wound;
    transforming said endogenous alternating electrical signal into a voltage versus frequency spectrum using a Fast Fourier Transform (FFT) algorithm; and
    diagnosing said wound as a chronic wound when the voltage for a frequency between 65-200 Hz of the frequency spectrum is below $10^{-7.3}\pm10\%$ volts and as an acute wound when the voltage for a frequency between 65-200 Hz of the frequency spectrum is above $10^{-7.3}\pm10\%$ volts.

11. The method of claim 10, wherein the detecting and recording of said endogenous alternating electrical signal and the transforming of said endogenous alternating electrical signal into a voltage versus frequency spectrum are performed by using at least one signal processor.

12. The method of claim 11, wherein the detecting and recording of the endogenous alternating electrical signal in the area of the wound further comprises placing at least two electrodes in the vicinity of the wound, wherein the at least two electrodes are operatively coupled with the at least one signal processor.

13. The method of claim 12, wherein the placing of the at least two electrodes comprises placing the at least two electrodes on opposing sides of the wound.

14. The method of claim 12, wherein the placing of the at least two electrodes comprises placing the at least two electrodes on the opposing and most distant sides of the wound.

15. The method according to claim 10, further comprising determining a therapy for the wound based on the diagnosing of said wound as a chronic wound or as an acute wound.

16. The method of claim 15, wherein the therapy is an electrical therapy.

17. The method of claim 10, further comprising delivering electrical currents to the wound when the wound is diagnosed as a chronic wound.

18. The method of claim 10, wherein the electrical currents are selected from the group consisting of: alternating electrical currents and pulsed electrical currents.

19. The method of claim 10, wherein the diagnosing of the wound comprises diagnosing the wound as a chronic wound when the voltage for a frequency between 100-150 Hz of the frequency spectrum is below $10^{-7.3} \pm 10\%$ volts and as an acute wound when the voltage for a frequency between 100-150 Hz of the frequency spectrum is above $10^{-7.3} \pm 10\%$ volts.

20. The method of claim 10, wherein before and during the detecting and recording of the endogenous alternating electrical signal, no electrical stimulation is applied to the patient.

\* \* \* \* \*